(12) United States Patent
Raghavan et al.

(10) Patent No.: US 7,231,075 B2
(45) Date of Patent: Jun. 12, 2007

(54) METHOD FOR DYNAMIC CHARACTERIZATION OF DENSITY FIELDS IN A COMPOUND STRUCTURE

(75) Inventors: Raghu Raghavan, Baltimore, MD (US); Timothy Poston, Singapore (SG); John Kucharczyk, Novato, CA (US)

(73) Assignee: BrainLAB AG, Feldkirchen (DE)

( * ) Notice: Subject to any disclaimer, the term of this patent is extended or adjusted under 35 U.S.C. 154(b) by 63 days.

(21) Appl. No.: 11/063,662

(22) Filed: Feb. 23, 2005

(65) Prior Publication Data

US 2005/0265589 A1    Dec. 1, 2005

Related U.S. Application Data

(63) Continuation of application No. 09/745,039, filed on Dec. 20, 2000, now abandoned.

(51) Int. Cl.
*G06K 9/00* (2006.01)
(52) U.S. Cl. ........................ 382/128; 600/423
(58) Field of Classification Search ............... 382/128; 600/411, 423; 604/246; 250/370.07
See application file for complete search history.

(56) References Cited

U.S. PATENT DOCUMENTS 5,964,705 A * 10/1999 Truwit et al. ............... 600/423
6,061,587 A * 5/2000 Kucharczyk et al. ....... 600/411

* cited by examiner

*Primary Examiner*—Jingge Wu
*Assistant Examiner*—Tom Y. Lu
(74) *Attorney, Agent, or Firm*—Renner, Otto, Boisselle and Sklar, LLP

(57) ABSTRACT

A method supplies a dynamic vector map of properties within a region or a unified suite of quantification functionality for property functions, such as density functions, conduction functions (e.g., thermal conduction, electrical conduction, atomic or subatomic mass conduction, macromolecular mass conduction), defined on, defined in or defining a three-dimensional space, which functions may optionally vary in time. At least two services assisting in the definition of the map or suite, even in a dynamic modality, are selected from: (a) computation of the volume of the region where the density lies above or below a specified threshold, or between two specified values; (b) computation of the integral of the density; (c) estimation of the rate of change of the density with respect to time, optionally restricted to a specified region; (d) estimation of the local or global failure of conservation represented by changes with time in the density; (e) estimation of the local or global rate at which material with a changing density is passing through a specified surface (e.g., boundary); and (f) separation of the density of a material with a changing density, given an implemented transport model, into "free" and "bound" densities.

38 Claims, 14 Drawing Sheets

US 7,231,075 B2

METHOD FOR DYNAMIC CHARACTERIZATION OF DENSITY FIELDS IN A COMPOUND STRUCTURE

This application is a continuation of U.S. patent application Ser. No. 09/745,039 filed on Dec. 20, 2000 now abandoned, which is hereby incorporated herein by reference in its entirety.

BACKGROUND OF THE INVENTION

1. Field of the Invention

The present invention relates to the field of characterizing the properties of a field, particularly to the characterization of properties within a field relating to mass transfer or material movement. The characterization of field properties is related to fields such as localized absorption/adsorption of materials to surfaces or volumes, especially in the delivery of bioactive materials to in vivo tissue during therapeutic treatments.

2. Background of the Art

It is a routine procedure in image processing to "segment" a two-dimensional (2D) or three-dimensional (3D) image. This can be performed, for example, on 1) a photograph of a slice of biological material, or 2) a scan by computer-aided tomography (CAT), magnetic resonance imaging (MRI), sonogram, or seismology recordation systems, where the data resembles a stack of slices. Many ways of gathering such data exist in various areas of technology, such as, for example, scanning data from individual components in an image to provide distinct layers with related data (e.g., only single colors, only ranges of optical density, etc.).

The image provided in such segmenting comprises a rectangular array of points with specified intensity, density or color values, the points being called "pixels" in 2D and "voxels" in 3D. The objective of the segmentation procedure is to classify these points into classes of materials so that information can be read into or from the image. In a specialized technological field, such as in medical applications, for example, "bone", "muscle", "blood", or "tumor" may be assigned to different points and ultimately areas of the image. In geology, the classes might be "granite", "shale", "water", etc., and so on for other sciences. The typical starting point for classification of the image is the value attached to a specific point. For example, bone absorbs X-rays more than any other tissue, so that one can fix a threshold value T according to the scaling of a particular Computed Axial Tomography (CAT) image and use "opacity greater than I" as a test for attaching the label "bone" to a point. A "segment" is then either a) the class of points so classified, or b) a connected component of this class. For example, it can be useful in medical applications to recognize the left kidney and the right kidney as separate segments of the body. Various methods also exist for correcting errors and noise in the image. For example, an isolated voxel with a value associated with muscle, surrounded by voxels classifiable as bone, should usually be labeled as bone also.

There exists also a large range of software to assist humans in segmentation, allowing them to draw curves around a region so that the regions can be recognized as separate. For example, where a region presses closely against another region with similarly associated values (such as a bone touching a bone), single values alone would be inadequate for classifying points. Despite such software assistance, this region recognition technology is labor intensive, especially in 3D where the classification is usually done slice by slice. Therefore, improved automation is a continuing area of vigorous research. We assume herein that it is desirable that segmentation includes not only a labeling of grid points by segments, but also that some descriptive geometric information such as bounding areas such as its bounding box (the smallest rectangular region with sides parallel to the x, y and z axes that contains every point of it) or a list of boxes in some scheme such as an octree division of the grid is provided, so that between all of these components of the segmentation labeling system, all of the points of the segment are included and identified (classified). Such additional data allow iteration over a shorter sequence of grid points than the whole set, when points outside the segment will contribute nothing to the intended result of the classification within the segmentation. Where such data are not delivered with the segmentation, they can be rapidly constructed for the entire segment list by a single run-through of the grid. Therefore, we assume that they are available.

Once 3D segmentation is achieved, it allows volumetry, the defining and/or measuring of the volume of a segment, which is proportional to the number of voxels labeled as belonging to it. This can be important either in static images, such as a geological or body scan where it answers questions like "How much ore is present?" or "is the liver enlarged?" or in a sequence of 3D images, such as a record of a beating heart, where the change in volume of the left ventricle can assist in quantifying what fraction of the blood is expelled into the aorta, and thus how effectively the heart is functioning as a pump. As a point is either In or Out of a segment (it is or is not blood, muscle, granite, etc.), volumetry techniques have developed for this two-valued context. The present invention addresses the computation of quantities appropriate to, and by methods appropriate to, continuous-valued variables such as a density or concentration.

SUMMARY OF THE INVENTION

A method that supplies a unified suite of quantification functionality for density functions defined on or defining a three-dimensional space, which may optionally vary in time, includes at least two services assisting in the definition. These services may include in a dynamic modality:

(a) Computation of the volume of the region where the density lies above or below a specified threshold, or between two specified values.
(b) Computation of the integral of the density (that is, determining a total amount of material within the region).
(c) Estimation of the rate of change of the density with respect to time, optionally restricted to a specified region.
(d) Estimation of the local or global failure of conservation represented by changes with time in the density, whether or not the method is given an implemented transport model.
(e) Estimation of the local or global rate at which material with a changing density is passing through a specified surface (e.g., boundary), whether or not the method is provided with an implemented transport model.
(f) Separation of the density of a material with a changing density, given an implemented transport model, into "free" and "bound" densities.

The present invention does not address the static segmentation of an image into classes, as described above. Rather, the invention assumes such a classification to have been completed, if needed. The present method addresses the dynamic volumetry of a first material diffusing or being otherwise transported through another substance (e.g., the medium or environment through which the diffusing material is passing), that substance through which materials are being transported may be, by way of non-limiting examples only, a compound structure such as a brain, terrain, waterway, habitat or mountain. We refer to the latter substance, whether simple or compound, as the substrate. Various methods have recently made it possible for scanning systems to estimate the densities c of such a substance at a grid of positions (x, y, z), such as labeling drugs for MRI visibility (e.g., U.S. Pat. Nos. 6,061,587 and 6,026,316) or attaching green fluorescence protein (GFP) that makes the material glow under suitable conditions. Equally, such an array c (x, y, z) of scalar values c (x, y, z) may arise from a simulation of a transport process, often for purposes of simulation, as in [Copending U.S. patent Application bearing attorney's docket number 723.032US1, titled "A METHOD AND APPARATUS FOR TARGETING MATERIAL DELIVERY TO TISSUE" baring U.S. Ser. No. 09/566,478, filed May 8, 2000]. It may also come from the evaluation at grid points of an algorithmically specified function: for example, the most concise specification of "the ball of radius R centered on (X, Y, Z)" is as the set of points (x, y, z) where c (x, y, z)=$((x-X)^2+(y-Y)^2+(z-Z)^2)/R^2$ does not exceed 1. This is an implicit specification, defined by a testable criterion rather than by a finite or infinite list of points. With more complicated functions, c, implicit functions are widely used in computer-aided design (CAD). The present invention may be applied to such c also, allowing (for instance) efficient calculation in CAD of both volumes and—where constant or variable mass density is known—weight. Throughout this document, the symbol c refers to a scalar quantity (number) for which possibly different values exist at a plurality points in space and where appropriate at a plurality of times. (That is, c is a function of position or of position and time.) Sometimes the plurality of points at which values are available is continuous, sometimes it is restricted to a grid of points indexed by integer triples (i,j,k) with indices lying in a specified range, at a fixed time or at a finite plurality of times. (This may arise by storage of an array of c values at such a grid found by physical scanning, or by evaluation at grid points of a function defined on arbitrary points, at the said fixed time or plurality of times.) Where it is necessary to emphasize that c is available only at grid points, with values stored in an array (which then formally constitutes the function produced by restricting c to the set of those grid points), we distinguish it as $c_g$. If c is a temperature in tissue subjected to electromagnetic fields in an imaging system, the present invention applies to such questions as "what fraction of the hippocampus is heated to a temperature above 38° C.?" If c (x, y, z) is the heating rate at (x, y, z), we may wish to compute total heat input, and so on.

For generality, therefore, we refer to c (x, y, z) or c (x, y, z, t) as a density, and to the material, heat, rate or other real or formal quantity that c describes as a superstrate.

The present invention applies to all situations in which such a grid $c_g$ of c (x, y, z) information can be estimated during dynamic variations in the superstrate. The interest is particularly in the case in which the superstrate is moving, so that repeated scans provide a sequence of changing value grids, that is a dynamic image of the material (condition, property, etc.) and its relationship within the superstrate. Note that the signal strength found by the material detection system is not always linearly proportional to the density, but as long as the measured quantity changes monotonically with the density and has a consistent value at each density, c can be deduced from it. We assume such pre-processing to have been done, and work with a grid $c_g$ of density estimates c. In certain cases the scanning system can distinguish between bound states of the superstrate, where the superstrate is attached to a particular point of the substrate, and free states, where the superstrate can move through the substrate. In such cases, we distinguish the bound density $c^b$ from the free density $c^f$. Often a superstrate has a desired therapeutic effect, or an undesired effect, only when its density lies between certain limits. It is thus useful to quantify the volume of substrate in which c or $c^b$ or $c^f$ is within such a range.

Given an estimate $c_g$ of the density c, or $c^b$ and $c^f$, the present invention computes (i) the overall volume of the region in which c or $c^b$ or $c^f$ lies between user-specified limits $C_{low}$ and $C_{high}$, (ii) the total amount of superstrate, (iii) the rate at each point at which the superstrate is being created ex nihilo or from other distributed entities not contributing to the estimates c, $c^b$, or $c^f$, less the rate at which it is being destroyed, with or without production of other entities, (iv) the total rate at which the superstrate is being created, less the rate at which it is being destroyed, (v) where the scanning technology permits, the separate totals of free and bound superstrate, (vi) the rate at each point at which the superstrate is being bound, less the rate at which it is being freed at that point, (vii) the overall rate of binding less freeing of the superstrate, (viii) the rate at which the superstrate is leaving or entering the scanned region through each point on its surface, and/or (ix) the overall rate at which the superstrate is leaving or entering the scanned region. The present method further computes for any user-selected region, S, the corresponding restricted quantities (I) the overall volume of the region within S in which the density lies between user-specified limits $C_{low}$ and $C_{high}$, (II) the total amount of superstrate with S, (III) where the scanning technology permits, the separate totals of free and bound superstrate within S, (IV) the total rate at which within S the superstrate is being created ex nihilo or from other materials not contributing to the estimate c, less the rate at which it is being destroyed, (V) the overall rate within S of binding less freeing of the superstrate, (VI) the rate at which the superstrate is leaving or entering S through each point on the surface of S, and/or (VII) the overall rate at which the superstrate is leaving or entering S.

Given a segmentation of the scan region that is spatially registered with the density scan (and in the case of a sequence of segmented scans of a moving structure or superstrate or sub-component therein, temporally registered also), the region S can be a segment such as a tissue T, allowing the system to report such quantities as "total material in the hippocampus".

BRIEF DESCRIPTION OF THE DRAWINGS

Drawing 1 shows a sum of values serving as an approximate integral.

Drawing 2 illustrates that a piecewise linear fit to data points gives a different estimated integral than a spline fit.

Figure 1:
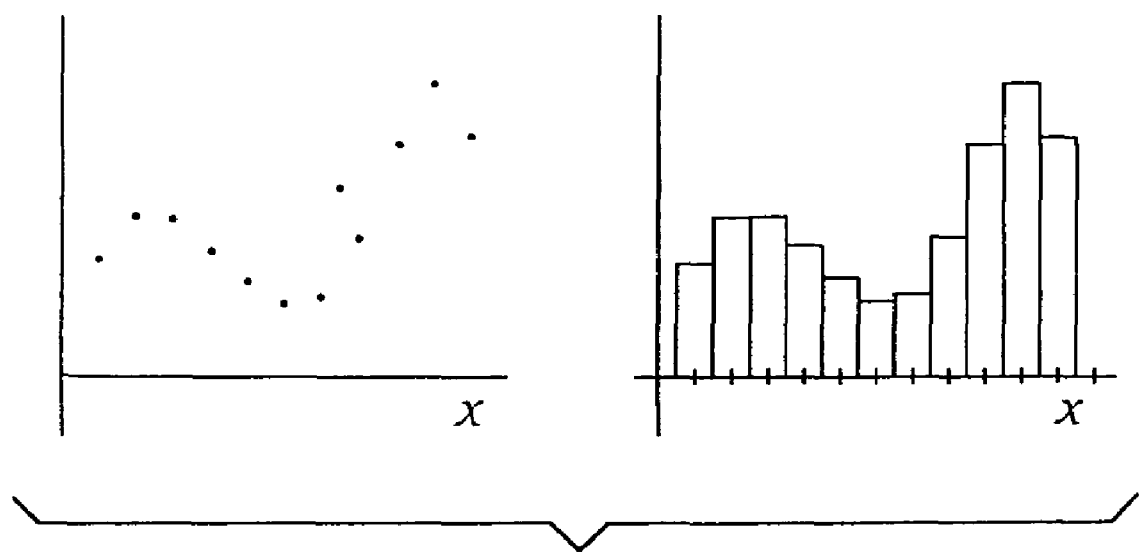
Figure 2:
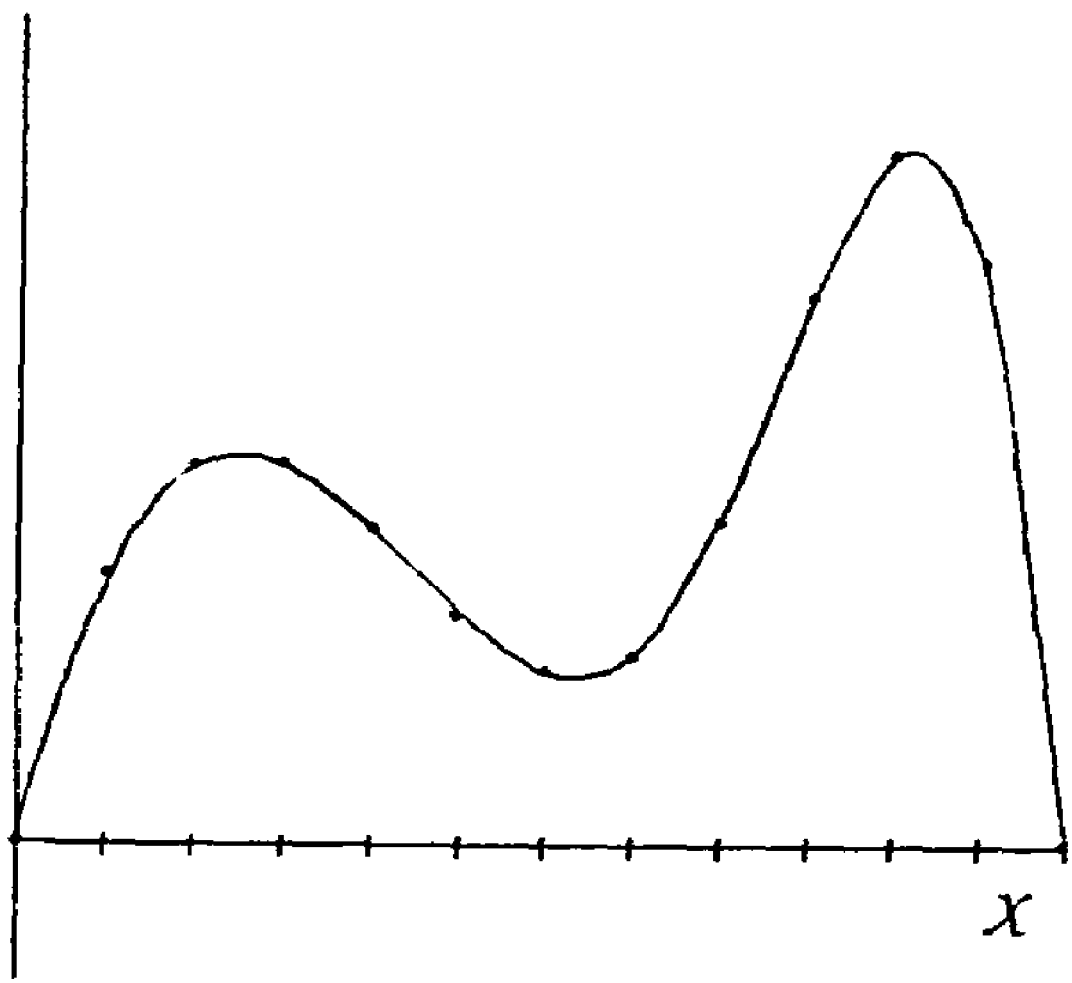
Figure 3:
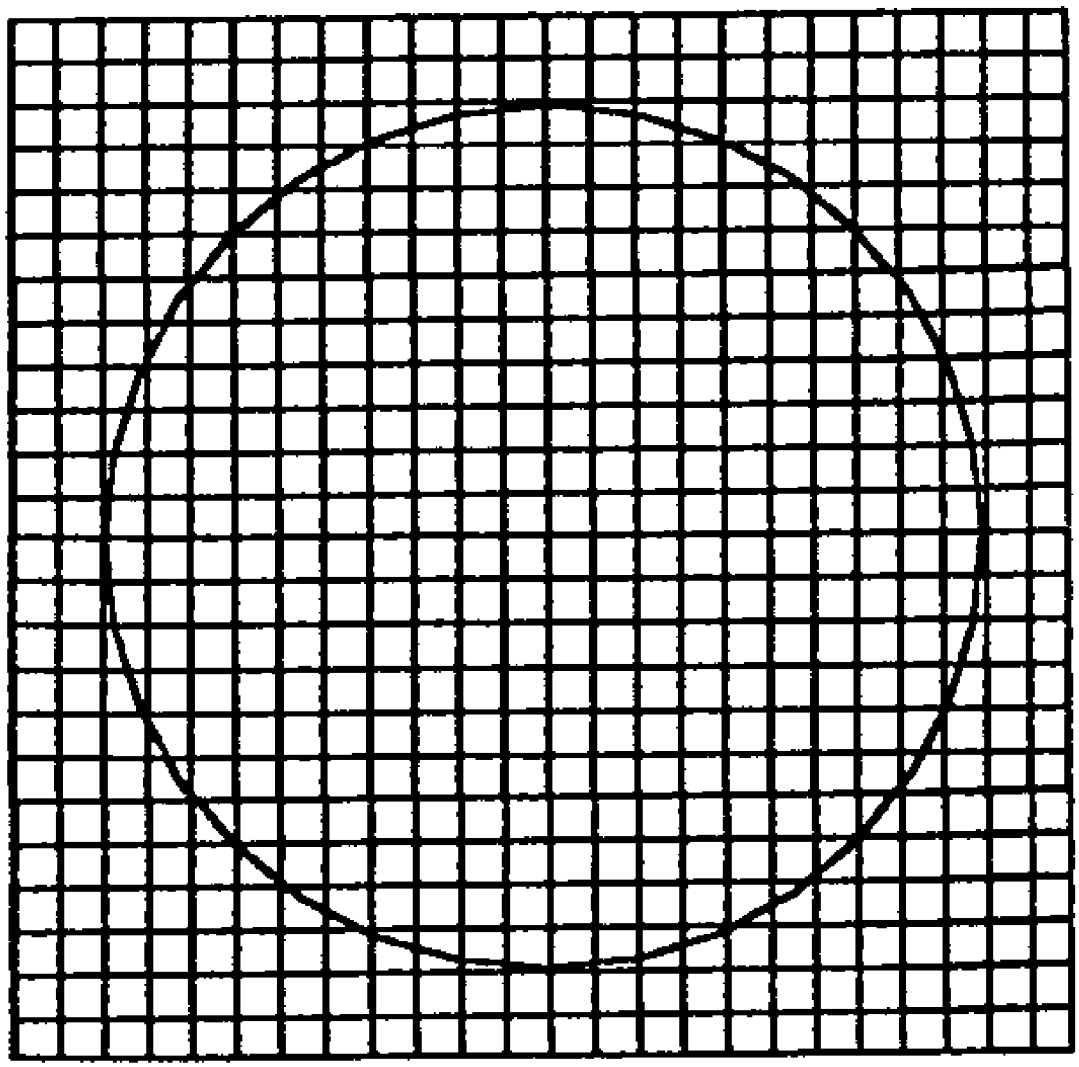
Figure 4:
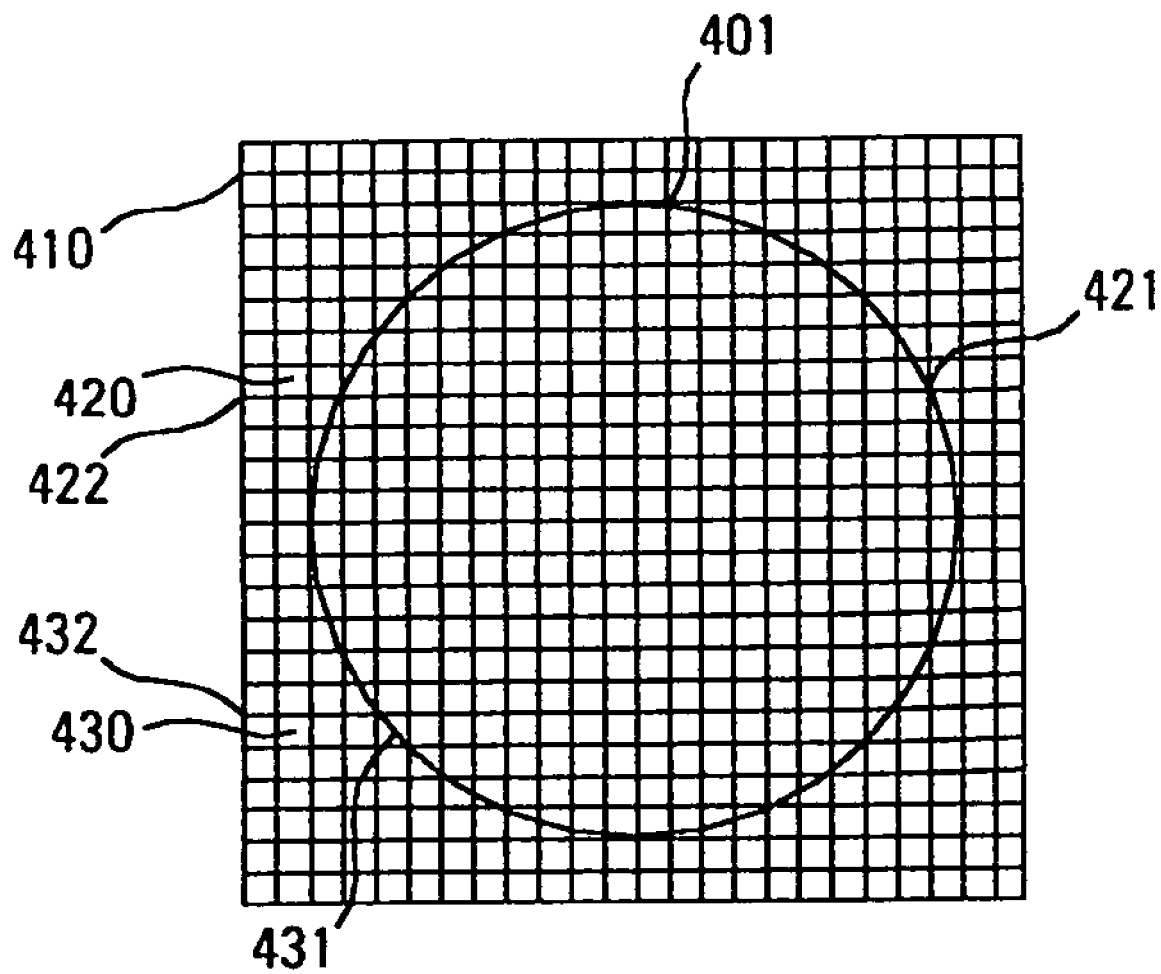
Figure 5:
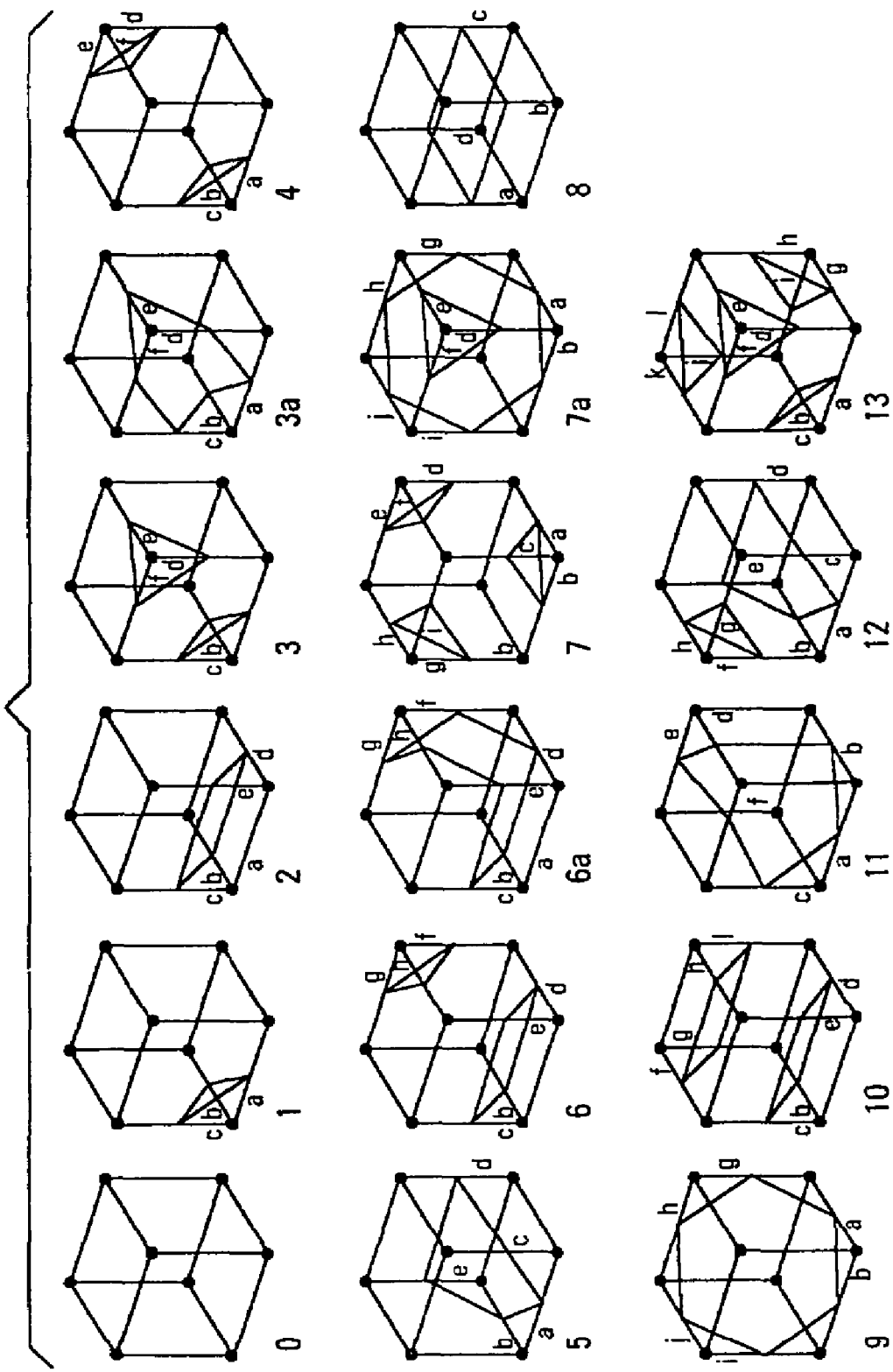
Figure 6:
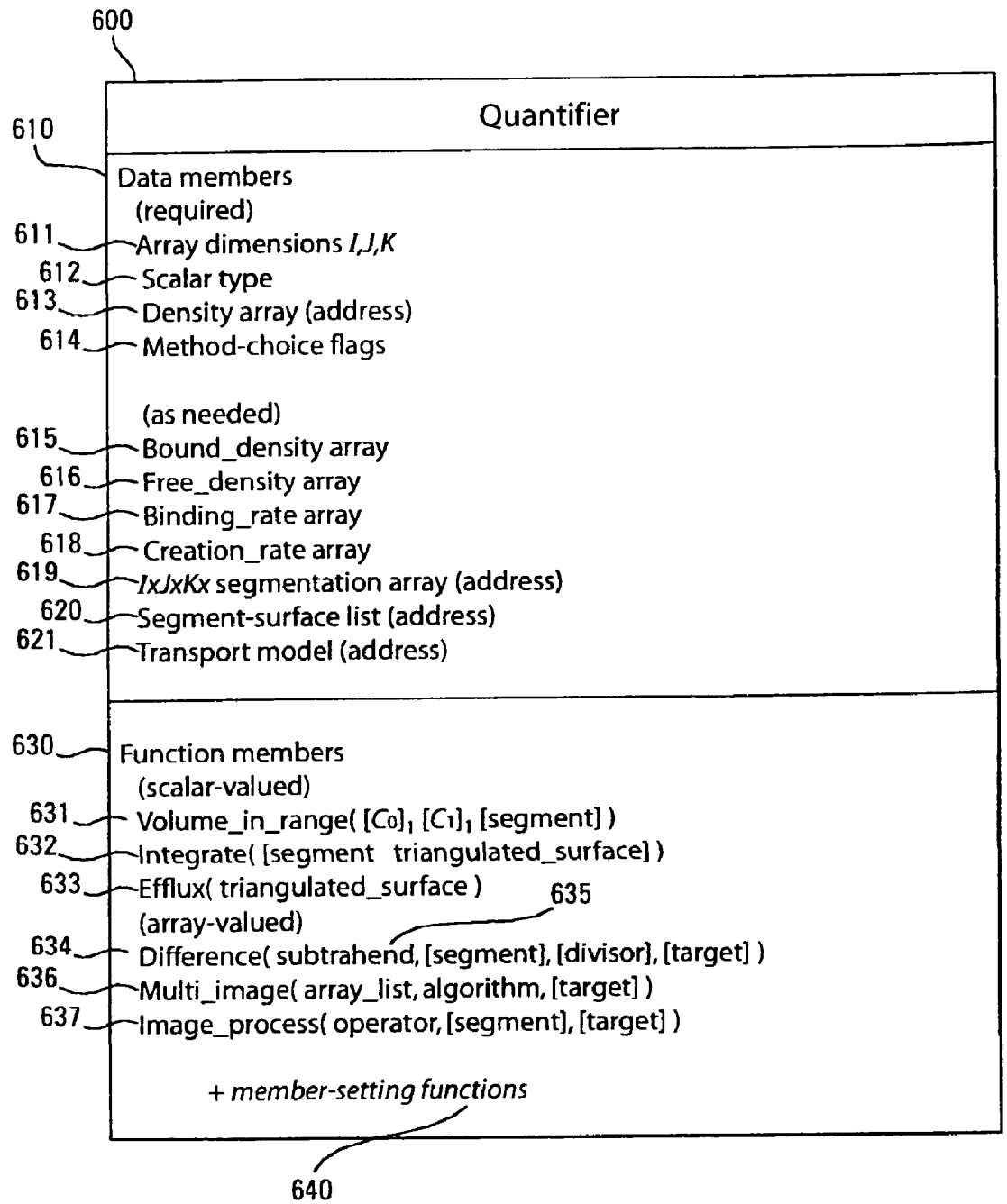
Figure 7:
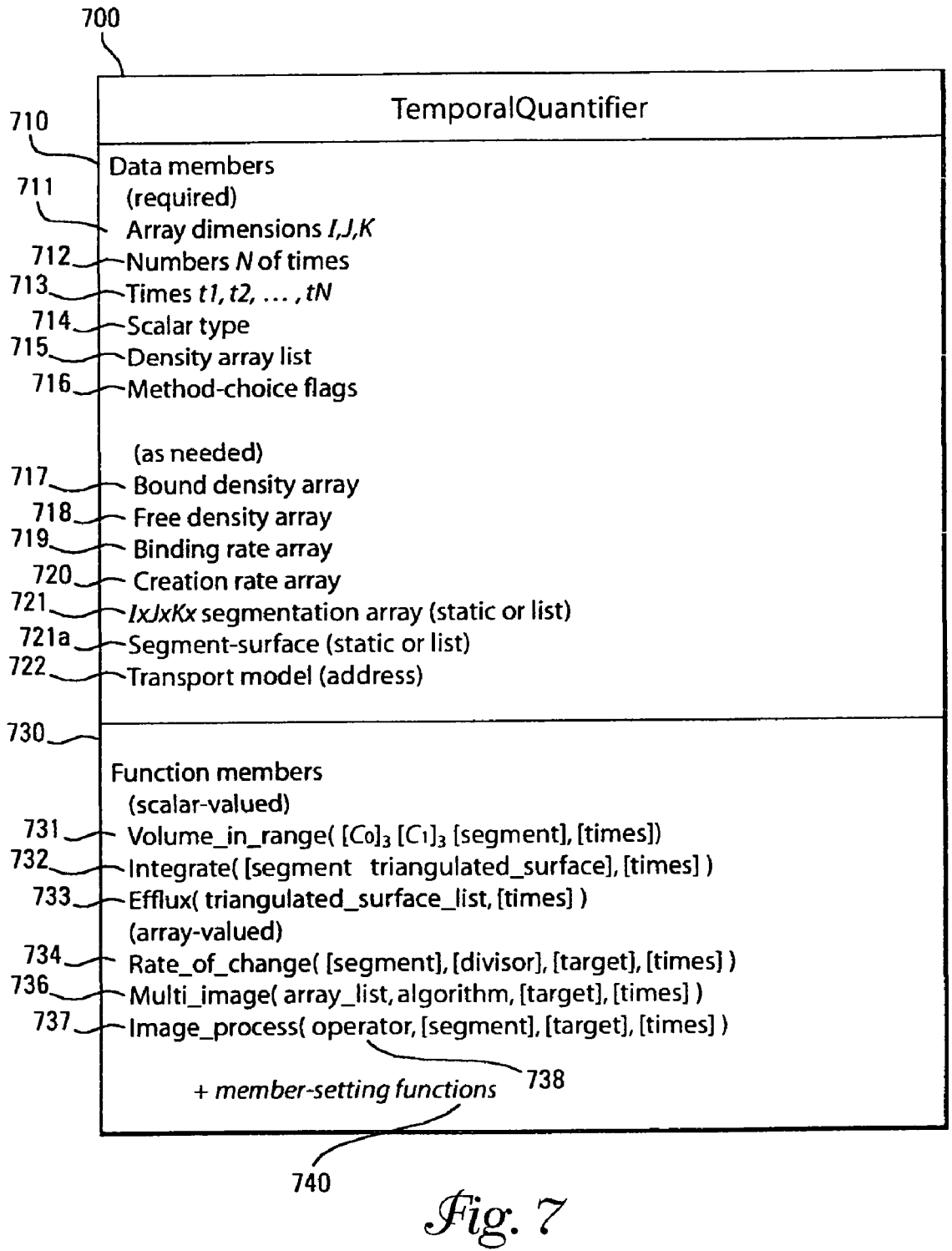
Figure 8:
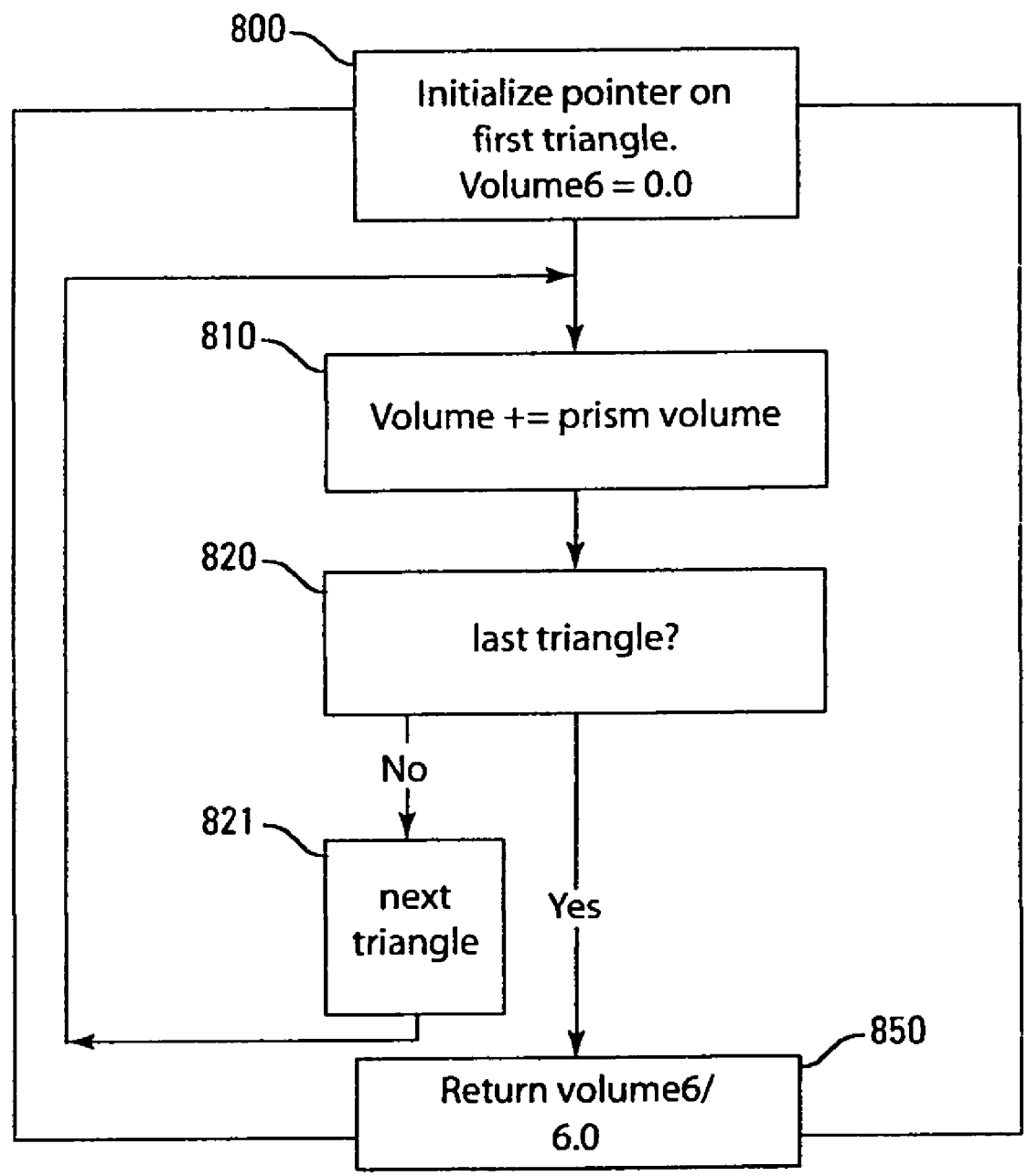
Figure 9:
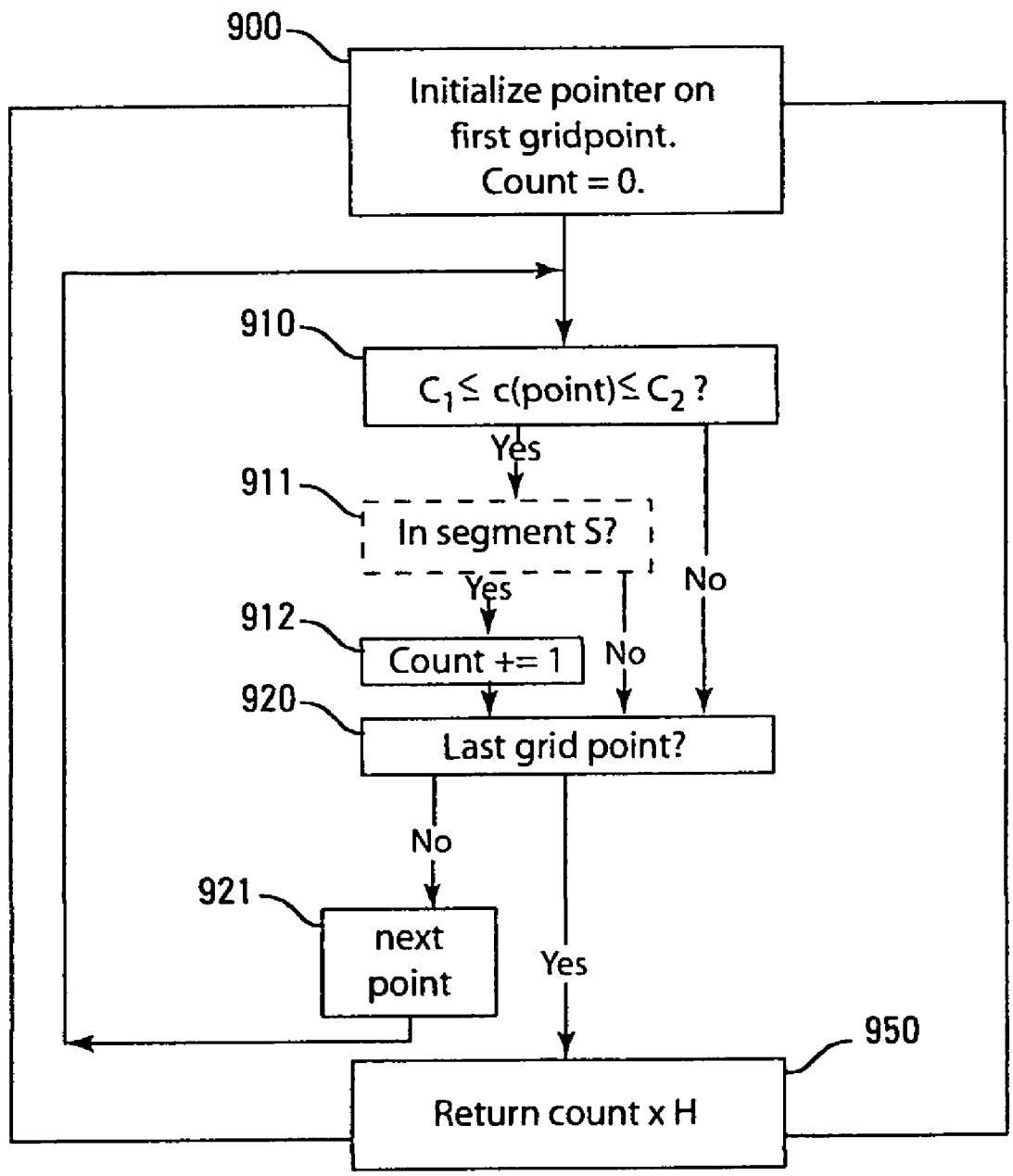
Figure 10:
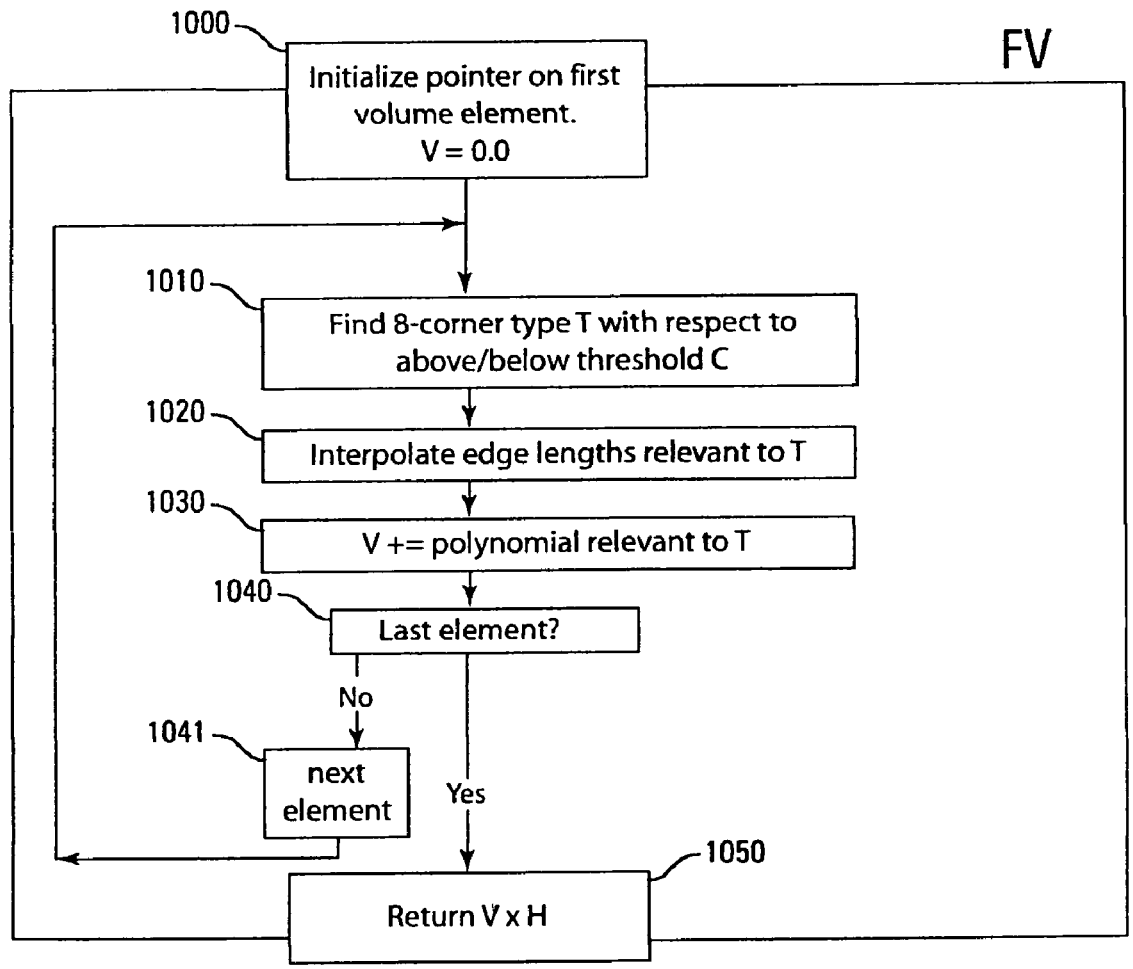
Figure 11:
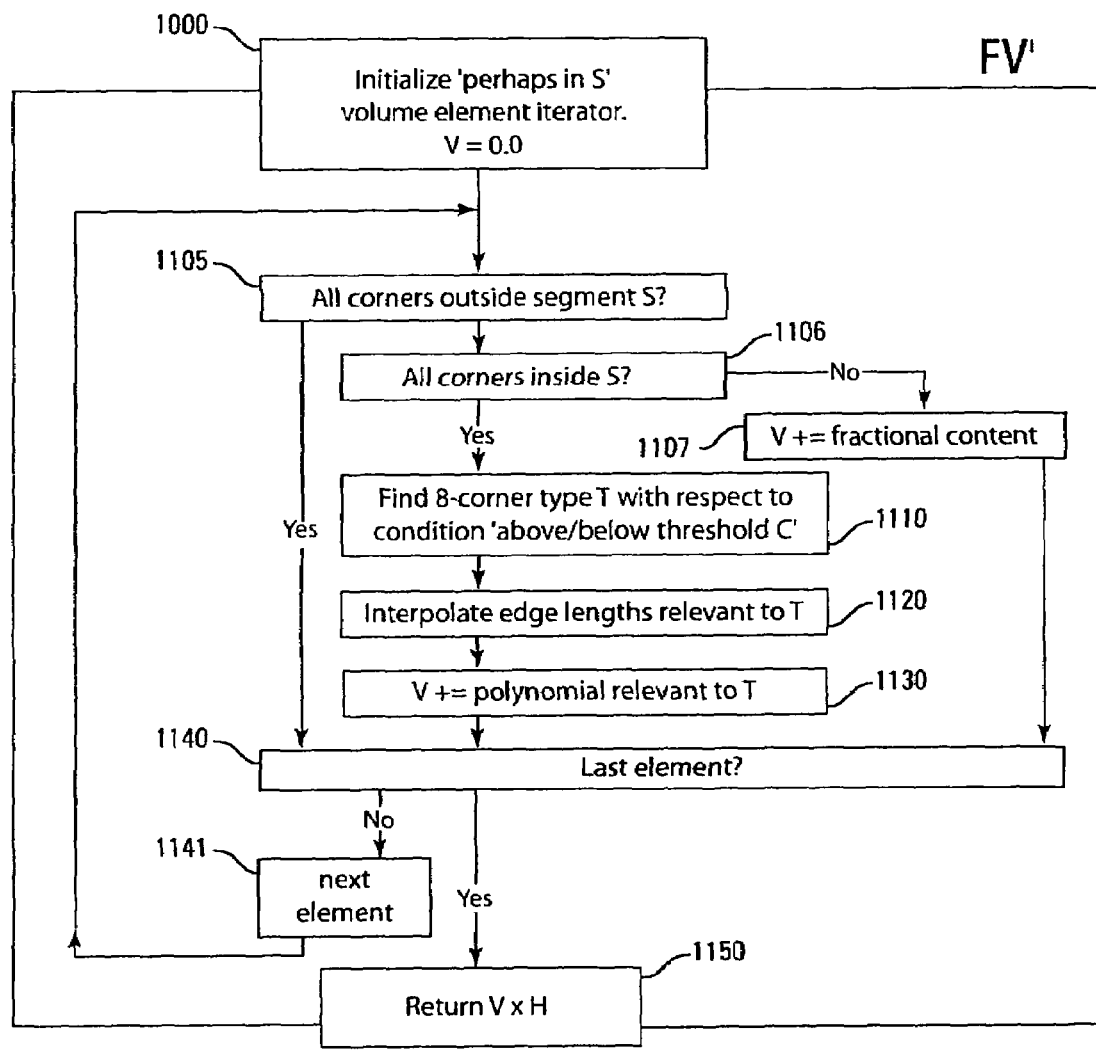
Figure 12:
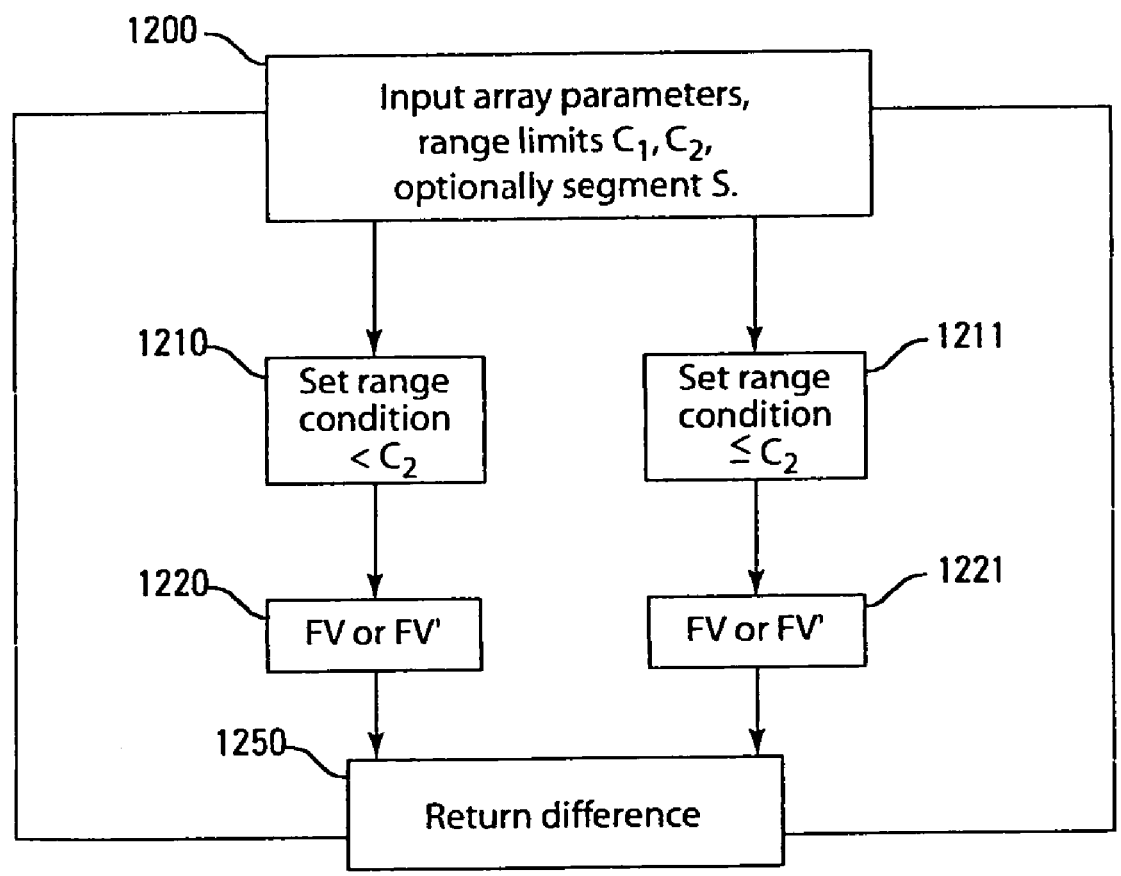
Figure 13:
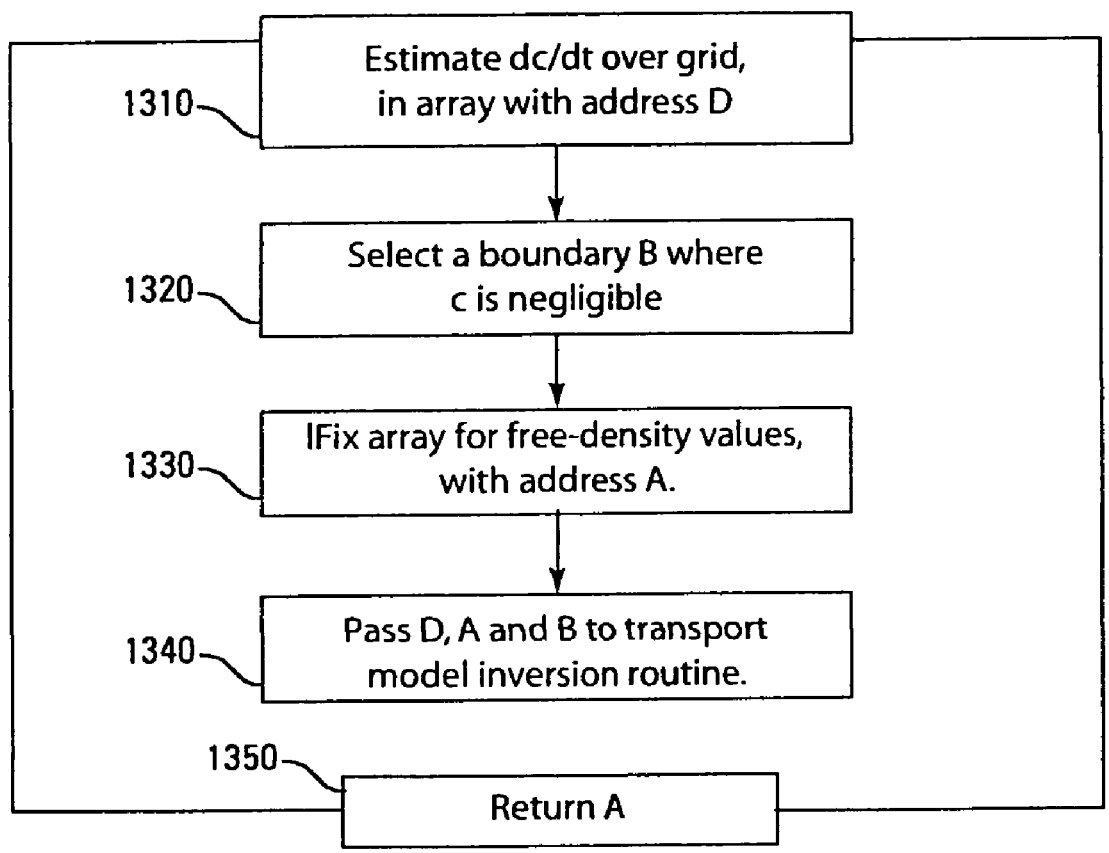
Figure 14:
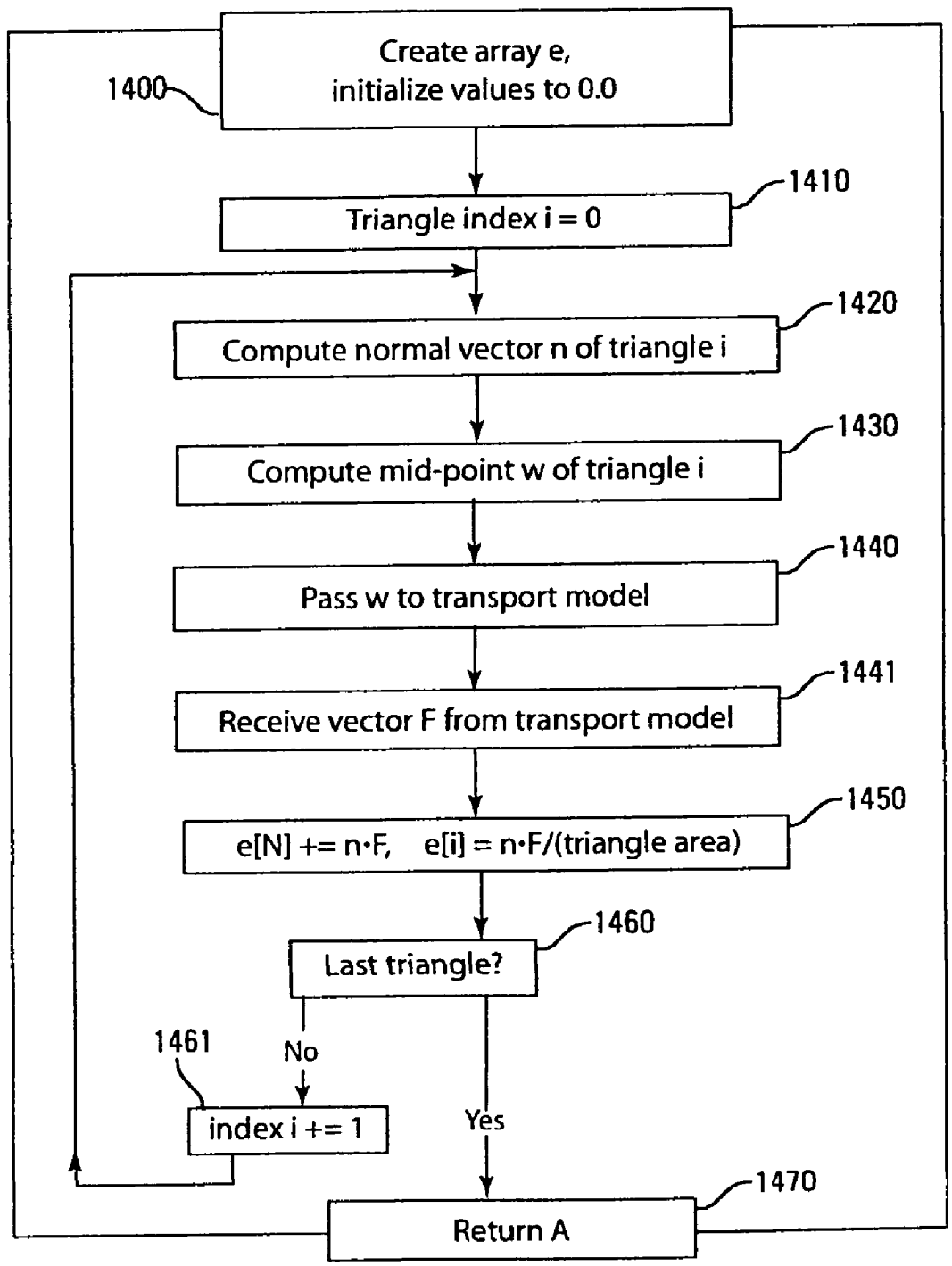

Drawing 3 illustrates the error in estimation of content (area or volume) by counting grid points.

Drawing 4 illustrates a method using regions tipped by pieces of boundary.

Drawing 5 shows the distinct ways (up to rotation and in/out exchange) that a volume boundary can meet the edges of a volume element.

Drawing 6 shows the data and function members of the object class that delivers the time-independent functionality of the invention.

Drawing 7 shows the data and function members of the object class that delivers the time-dependent functionality of the invention.

Drawing 8 shows the logical flow of the computation of the volume enclosed by a set of triangles.

Drawing 9 shows the logical flow of a coarse, fast estimate of the volume in which the density lies between limits C, and $C_2$.

Drawing 10 shows the logical flow of a more precise estimate of the volume in which the density lies above or below a threshold C.

Drawing 11 shows the logical flow of a version of the corresponding estimate of the volume within a segment S in which the density lies above or below a threshold C.

Drawing 12 shows the use of the logic in Drawing 10 or 11 to give the corresponding estimate of the volume within a segment S in which the density lies between limits $C_1$ and $C_2$.

Drawing 13 shows the logical flow of the computation of a free density from a free-plus-bound density and a transport model.

Drawing 14 shows the logical flow of the calculation of net efflux through a triangulated surface.

DETAILED DESCRIPTION OF THE INVENTION

A method supplies a dynamic vector map of properties within a region, or as otherwise stated, a unified suite of quantification functionality for property functions, such as density functions, conduction functions (e.g., thermal conduction, electrical conduction, atomic or subatomic mass conduction, macromolecular mass conduction), defined on, defined in or defining a three-dimensional space, which functions may optionally vary in time. The method should include at least two services assisting in the definition of the map or suite. These services may include as non-limiting examples, in a dynamic modality:

(a) Computation of the volume of the region where the density lies above or below a specified threshold, or between two specified values. This type of service assists in providing a basis for characterizing a point or region where a property (e.g., density) can be a part of the definition of the substrate.

(b) Computation of the integral of the density (that is, determining a total amount of material within the region). This provides a basis for establishing a foundation for comparison of changes within the region, as a starting point for determining changes must begin with an initial or ground state value.

(c) Estimation of the rate of change of the density with respect to time, optionally restricted to a specified region. Rate functions are critical in determining dynamic properties for mapping. The rate may be with respect to concentration changes, conductivity rates, temperature changes, optical density changes, viscosity changes, or any other observable property.

(d) Estimation of the local or global failure of conservation represented by changes with time in the density, whether or not the method is given an implemented transport model. This service can identify changes indicating events wherein the total superstrate amount does not remain constant within the region or volume. This could be evidence of mass transfer out of the region, destruction or creation of material within the region (e.g., expression or metabolism), and other events that alter the integrated totality of measured substrate within the region.

(e) Estimation of the local or global rate at which material with a changing density is passing through a specified surface (e.g., boundary), whether or not the method is provided with an implemented transport model. This service is an indication of transfer rates between segments within the region, as between solid surfaces and moving liquid mass in contact with the surface.

(f) Separation of the density of a material with a changing density, given an implemented transport model, into "free" and "bound" densities.

We assume that a scanning system (hardware and software), simulation, or function sampling delivers a grid $c_g$ of density estimates $C_{ijk}$ at points rectangularly arranged in space, for integer values $0 \leq i < I$, $0 \leq j < J$ and $0 \leq k < K$, with positions $(x, y, z) = (ih_x, jh_y, kh_z)$ in a suitably chosen system of rectangular coordinates. The ranges of the integers i, j and k may begin other than with 0, and one skilled in the art may easily extend the application of the present invention to the case where the region sampled is not rectangular, but since a rectangular array of points in a cuboidal region is overwhelmingly typical for the presentation of scan data, we use this case for exposition. Similarly, the points may be arrayed in the face-centered cubic lattice arrangement typical of the centers of stacked cannonballs, or according to any other regular scheme, without materially altering the application of the present invention. Other equivalent volumetric formats for analysis may also be used, such as spherical arrays or regions, pyramidal arrays or regions, or any other geometric formats or mathematical formats. There does not at this time appear to be any reason for assuming significant benefits in the practice of the invention for using formats other than cubic, rectangular or spherical regions, but the others may be used as a form of equivalent which might prove to be desirable because of the shape or certain three-dimensional volumes that are being considered in specific applications of the process to a patient or treatment. Mixtures of volumetric formats and regions may, of course, also be performed and used in the practice of the invention, especially where tighter fit (higher accuracy) is desired and the software can select from amongst different shapes and formats to determine best approximations of volumetric fits.

Superstrate Quantification

We denote the region sampled as R, and assume that the amount (volume, mass, conductivity, adsorptivity, energy, or any other property or characteristic) of superstrate within R is the integral over R of the density c, of which the data grid $c_g$ provides estimates $c_{ijk}$ only at grid points. A simple estimate of this integral is given by $$h_x h_y h_z \sum_{\substack{i=0 \\ j=0 \\ k=0}}^{\substack{I-1 \\ J-1 \\ K-1}} c_{ijk} \quad (1)$$

since $h_x h_y h_z$ is the volume in (x, y, z)-space of the cuboidal volume element of points nearer to a given $(x, y, z) = (ih_x, jh_y, kh_z)$ than to its neighbors in the grid. In one dimension, this corresponds to estimating the integral of a function f(x) by a sum of the values $c_i = f(ih)$, $$h \sum_{i=0}^{I-1} c_i, \qquad (2)$$

which assumes that f has a bar-chart graph as shown in Drawing 1, and sums the areas of the bars. An alternative approximation $\tilde{f}$ to f is to interpolate linearly between the sample points and find the area $$\frac{h}{2} \sum_{i=0}^{I-1} (c_{\bar{i}} + c_i) \text{ where } \bar{i} = i + 1 \qquad (3)$$

under the resulting polygonal curve, but the result is identical except that (2) extrapolates for half a step beyond the end points. If the end contributions are made proportional to the length element fraction that is not outside the end points, the result coincides with (3). Similarly, if we replace (1) by trilinear interpolation within each rectangular volume element whose edges are axis-direction steps in the sample array, the resulting estimate:

$$\frac{h_x h_y h_z}{8} \sum_{\substack{i=0 \\ j=0 \\ k=0}}^{\substack{K-1 \\ J-1 \\ I-1}} \left( c_{ijk} + c_{\bar{i}jk} + c_{h\bar{j}k} + c_{ij\bar{k}} + c_{\bar{i}j\bar{k}} + c_{\bar{i}\bar{j}k} + c_{i\bar{j}\bar{k}} + c_{\bar{i}\bar{j}\bar{k}} \right) \qquad (4)$$

agrees with (1) if the latter is adjusted to reflect the half, quarter and eighth volumes (within the grid) of the elements meeting the boundary.

However, if an f(x) known only by its values at step points is approximated by a smoother curve $\tilde{f}$ such as a cubic spline (Drawing 2), the area under $\tilde{f}$ (and hence the estimated total for f) is slightly different. This result is similar for smoother fits in three dimensions. This is pointed out only to observe that there are multiple means of estimating the total of a sampled density, of which the present invention may use any method for sampling density of the superstrate or the substrate. For simplicity, a preferred implementation is the use of (1), whose difference from other estimates is typically less than the uncertainty resulting from noise in the sampling process. The present invention is easily applied by one skilled in the art to the use of other estimation methods.

Volume Quantification

Defining a range function ρ as $$\rho_{p,q}(x) = \begin{cases} 1 & \text{if } p \leq x \leq q \\ 0 & \text{otherwise} \end{cases} \text{ or } \qquad (5)$$

$$\rho_q(x) = \begin{cases} 1 & \text{if } x \leq q \\ 0 & \text{otherwise} \end{cases} \text{ or } \qquad (6)$$

$$\rho_p(x) = \begin{cases} 1 & \text{if } p \leq x \\ 0 & \text{otherwise} \end{cases}, \qquad (7)$$

this provides a "density within range" volume $$\int_{(x,y,z) \in R} \rho(c(x, y, z)) dx\, dy\, dz \qquad (8)$$

which may be estimated in various ways for the purposes of the present invention. The simplest estimate is performed by counting the array points $(x, y, z)=(ih_x, jh_y, kh_z)$ for which $r(c_{ijk})=1$, equivalently summing the function $\rho(c)$. However, as Drawing 3 illustrates for the two-dimensional case of computing area rather than volume, this introduces unnecessary inaccuracy. The area $\rho r^2 \approx 3.1416$ of the set $\{(x, y) | x^2+y^2 \leq 1\}$ is poorly estimated as 3.17 by counting the 317 squares whose centers lie inside the circle. Several more accurate methods may be used. For some specific fields of use, this degree of inaccuracy would be acceptable, while with others it might not be tolerable.

In one alternative method, one first creates a piecewise linear description of the boundary of the range: in two dimensions a polygonal curve, in three dimensions a polyhedral surface. Drawing 4 shows the circular edge of the set $\{(x, y) | x^2+y^2 \leq 1\}$ approximated by an oriented loop 401 of twenty-four straight edges. Orienting this loop anticlockwise, the areas of strips joining each strip to a side 410 of the region R sum to the area inside the loop 401, if opposite signs are applied to strips like 420, where the edge 421 projects to an upward step 422 on the side 410, and strips like 430, where the edge 431 projects to a downward step 432. Analogously, suppose that the surface $\{(x, y, z) | f(x, y, z)=C\}$ is approximated by a closed set Σ of triangles, as may be done by the Marching Cubes algorithm (in Lorensen, W. E. and Cline, H. E., SYSTEM AND METHOD FOR THE DISPLAY OF SURFACE STRUCTURES CONTAINED WITHIN THE INTERIOR REGION OF A SOLID BODY, U.S. Pat. No. 4,710,876, 1987), the Skeleton Climbing algorithm (T. Poston, T-T. Wong, and P-A. Heng, "Multidirection Isosurface Extraction with Adaptive Skeleton Climbing, Computer Graphics Forum, 17, 3, September 1998, pp. 137–148; and T. Poston, H. T. Nguyen, P-A. Heng, and T-T Wong, "Skeleton Climbing: Fast Isosurfaces with fewer Triangles," Proceedings of Pacific Graphics '97, Seoul Korea, October 1997, pp. 117–126., or otherwise. If each triangular face σ∈Σ has vertices $$v_0(\sigma)=(x_0(\sigma), y_0(\sigma), z_0(\sigma))$$

$$v_1(\sigma)=(x_1(\sigma), y_1(\sigma), z_1(\sigma))$$

$$v_2(\sigma)=(x_2(\sigma), y_2(\sigma), z_2(\sigma)) \qquad (9)$$

so ordered that they appear anticlockwise when viewed from outside the surface, we may write the volume inside the surface as a signed sum of volumes of slant-topped prisms $$\sum_{\sigma \in \Sigma} ((x_1(\sigma) - x_0(\sigma))(y_2(\sigma) - y_0(\sigma)) - \qquad (10)$$

$$\frac{(x_2(\sigma) - x_0(\sigma))(y_1(\sigma) - y_0(\sigma)))(z_0(\sigma) + z_1(\sigma) + z_2(\sigma))}{6}$$

Note that if the set Σ meets the higher-z face of R, the area of the part of R within the volume (according to the approximation Σ of its boundary) must be included for a correct result. Topologically triangles could be included within any face of R met by the in-range volume, for a closed surface, but triangle within the sides and bottom contribute nothing to the volume sum (10) and may thus be omitted from the calculation.

The method above is an efficient volume computation where such a set Σ has already been constructed (for example, in order graphically to display the region where c is within the range of interest), but constructing Σ solely for this purpose represents unnecessary computation. In a further alternative method, we classify volume elements with corners on the sample grid according to the way their vertices meet the in-range and out-of-range values of c, and estimate the volumes of the within-range sets within them.

Drawing 5 shows different ways that the vertices of a volume element may be within range (shown as a full circle) or out of range (shown as an empty circle), with a corresponding simple polygonal curve in which the surface of the in-range set can meet the faces of the element, consistent with the data. This is similar to the classification in Lorensen, W. E. and Cline, H. E., "SYSTEM AND METHOD FOR THE DISPLAY OF SURFACE STRUCTURES CONTAINED WITHIN THE INTERIOR REGION OF A SOLID BODY," U.S. Pat. No. 4,710,876, 1987, hereinafter referred to as the Marching Cubes algorithm, but differs where a face is ambiguous, with exactly two corners within range and these are diagonally opposed. In an ambiguous face, we so choose the curve as to separate the in-range and not the out-of-range corners. Other consistent rules can be followed within the logic of the present invention. (For example, the opposite rule, or the rule that the curve length should be as short as possible may be used.) Every one of the 256 ways that the eight corners may between them be in or out of range is represented in Drawing 5, by a suitable rotation and/or a reversal of in-range and out-of-range, with reversal not permitted where there is an ambiguous face. (Permitting reversal in such cases would lead the original version of the Marching Cubes algorithm, as first described by Lorensen and Cline in the above-cited patent, to create triangle sets that are not as there claimed, separating surfaces between the in-range and out-of-range sample points.) It is not efficient in an implementation to determine to which of these cases an element may be reduced, and to rotate and/or reverse it to standard form, but it is more convenient here to show 17 cases rather than 256. Our preferred implementation uses a lookup table to find an appropriate transformed and implemented version of one of the formulas below, according to which of the 256 cases it represents.

The vertices of the polygonal curves shown in Drawing 5 lie on the element edges that cross between in-range and out-of-range sample points. Their position may most conveniently be estimated by linear interpolation between the sample values at the edge ends, but more complex procedures (such as those suggested in various papers elaborating marching Cubes) are usable within the framework of the present invention. For each such vertex, Drawing 5 labels the distance from one or the other neighboring sample point on the volume element edge.

There is no unique choice of surface spanning the polygonal curves in Drawing 5, but simple choices constructed from flat triangles and quadric quadrilaterals lead to the following formulas for the volumes contained by the surface within the volume element, all to be multiplied by the factor $h_x h_y h_z / 12$. Where a case not shown can rotate to a case in Drawing 5, the same formula applies: where reversal of in-range and out-of-range points is needed, the formula below should be subtracted from the number 12.

$0$ $2abc$ $(2(bc+de)+be+dc)$ $2(abc+def)$ $2(ab-abf+b+e-fb-fe+bc+ce+2dec-2de)$ $2(abc+def)$ $2(d-ae(8+b)+10(c+e)-9ac)$ $2(bc+de+fgh)+be+dc$ $2(6-hg(8+c)-b-d-c-bc+bg(c+f-1)-e-f+4g+3h+f(d-g)+gc+2hc+he)$ $2(abc+def+ghi)$ $2(5-b+ba(g-1)-g-i+ib-hg-ih+ij(h-1)-def)$ $3(a+d+b+c)$ $2(5-b+ba(g-1)-g-i+ib-hg-ih+ij(h-1))$ $2(bc+de+fg+ih)+be+dc+jh+gi$ $2(ac+af+f+e-ef+b-3be-ba+a+de)$ $2(d-ae(8+b)+10(c+e)-9ac+ghi)$ $2(abc+def+ghi+jkl)$ (11)

Where the desired volume is that of the points where c is between two limits $C_1 < C_2$, this algorithm may be used to find the volume below $C_1$ and subtract it from the volume below $C_2$, either volume element by volume element or as a total, depending on details of architecture and efficiency.

Transition Quantification

Superstrate density at a point (x, y, z) may change because superstrate moves, or because some transformation creates or annihilates the superstrate as a detectable entity with the scanning method currently in use. If the superstrate is a material inserted into the body with a "contrast agent" label whose detectability is constant (such as an atom that heavily absorbs X-rays, or a gadolinium atom visible to appropriately tuned MR imaging), only movement will be detectable. Certain labels will change frequency when their chemical configuration or chemical structure alters (as with F-19, Fluorine-19), and changes in MR response frequencies could then be used to assist in determination of changes in the state or volume of a specific compound, based upon the changing responses due to changes in chemical state of compounds with the label. (See, for example, the techniques used in copending U.S. Patent Application, titled "Imaging Methods For Visualizing Implkanted Living Cells," Inventors Michael Moseley et al., filed on Jun. 28, 2000, bearing U.S. Ser. No. 09/606,137, which imaging techniques and methods, particularly by Magnetic Resonance Imaging, are incorporated herein by reference.) For example, many applications of superstrate volumetry involve substances naturally created or destroyed by biological processes, and detectable by intrinsic properties. For example, the magnetic resonance response of an atom depends on its chemical situation. A hydrogen nucleus fixed in a large molecule is less free to rotate than one in a free water molecule, and this difference is one of the main contrast sources in MR imaging. Bound water, as in certain crystals, is distinguishable from free water. Ice is similarly distinguishable from free water, so that MR offers the possibility of sensors appropriate to control of cryogenics, managing the freezing of biological tissue to minimize damage.

With appropriately tuned MR pulses, such detectability may be made highly specific for nuclei in a particular molecular setting, thus making the MR scan a direct detector for a particular molecule in a particular state.

Given only a grid $c_g$ at discrete points (i,j,k) of samples or local estimates of a changing record c (x, y, z, t) at a sequence of times t, it is impossible to distinguish the net rate C (x, y, z, t) of creation (creation less destruction) of the superstrate with density c from the effects of superstrate transport. (In particular, it is logically allowable that all increments and decrements of c are due to local creation and destruction.) However, if the transport properties of the superstrate are known, we may write $$\frac{dc}{dt}(x, y, z, t) = (\text{net arrival}(x, y, z, t)) - C(x, y, z, t). \quad (12)$$

In the case of pure diffusion, for example, the arrival term is $D(x, y, z)\nabla^2 c(x, y, z, t)$, where the field D gives the diffusion tensor at each point. (In simple cases, this may reduce to a single constant, independent of position (x, y, z) and the direction of diffusion.) A copending patent application (see copending U.S. patent application Ser. No. 09/566,478, bearing, titled "A METHOD AND APPARATUS FOR TARGETING MATERIAL DELIVERY TO TISSUE" filed on May 8, 2000) describes how such terms may be established for a given substrate, with a model-dependent distinction between transport and destruction. (For example, when a drug diffusing in brain tissue may pass into veins and is removed by the blood flow, this may be treated as a "sink" rather than as explicitly modeled transport.) Where the arrival term is thus computable, the left hand side of (12) may be estimated from data, in general using some smoothing with respect to space and time since differences like $c_g(i,j,k,t_{next}) - c_g(i,j,k,t_{now})$ are more strongly affected by noise than are the estimates of c itself. The net creation rate C thus becomes a known scalar field such as c. The procedures described above can be applied to this, finding the total rate of creation by estimating its integral, the volume of the region in which creation occurs at a rate above some threshold, and so on. (In this case our "density" is a rate, and our "superstrate" is a process.)

In some applications, it is important to distinguish the bound density $c^b$ from the free density $c^f$. In some cases, the imaging technique may be tuned to this difference (for example, the binding of a molecule may change its nuclear resonance properties), so that $c^b$ and $c^f$ are directly detectable, and their volumetry may be handled separately by the methods above. In cases where superstrate is conserved, there is an alternative means of separation.

This alternative can be performed as for the transport dynamics applies only to the free density, so that $$\frac{dc^f}{dt}(x, y, z, t) = (\text{net arrival}(x, y, z, t)) - \text{binding rate} \quad (13)$$

$$\frac{dc^b}{dt}(x, y, z, t) = \text{binding rate} \quad (14)$$

$$\frac{dc}{dt}(x, y, z, t) = \frac{d(c^f + c^b)}{dt}(x, y, z, t) \quad (15)$$

$$= (\text{net arrival}(x, y, z, t))$$

Taking the case of diffusion transport as an example, the net arrival rate is $D(x,y,z) \nabla^2 c^f(x,y,z,t)$, so that for the transport operator $T = D(x,y,z)\nabla^2$:

$$Tc^f(x, y, z, t) = \frac{dc}{dt}(x, y, z, t) \quad (16)$$

where the right hand side is known by direct or indirect measurement. Given boundary conditions (such as a boundary on which c is zero, to which the superstrate has not yet diffused), knowledge of $\nabla^2 c^f$ implies a unique solution for $c^f$. The same is true for more general transport operators T, such as many of those arising in (the above mentioned attorney's docket number SLWK 723.032US1, titled "A METHOD AND APPARATUS FOR TARGETING MATERIAL DELIVERY TO TISSUE" U.S. Ser. No. 09/566,478, filed May 8, 2000). The data and logical structure information necessary to invert T are aspects of the transport model. For the purposes of the present invention, it is thus assumed that the transport model includes a function which, given access to a dc/dt value array on whose boundary c is negligible, fills another array with the solution of (16) for $c^f$.

Thus the values are available for $c^b = c^f - c$, and changes may be tracked in $c^b$ to give the binding rate. All these quantities may be separately displayed and integrated by the methods above. For computation, we replace the various c, $c^f$, $c^b$ by their corresponding grid estimates, and derivatives by the corresponding finite differences.

Segmented Superstrate Volumetry

Given a segmentation of the substrate (for instance into bone, white matter, gray matter, etc.), any of the above computations may be restricted to a user-selected segment S. In such a case the algorithm applies unaltered to each volume element that has all eight corners in S, and give 0 where all are outside S. In a doubly-boundary volume element E that contains a non-zero number of corners inside and corners outside S, and of corners above and below threshold, it is necessary to estimate the volume within E∩S that is on the desired side of the threshold. This may be done by various methods, according to the precision desired (since doubly-boundary elements are relatively few, the percentage impact on the total volume estimate is proportionally small). Most coarsely, one may multiply the estimate above by n/8, where n is the number of corners of E that are in S. More accurately, one may estimate the fraction of surface area of E that is in S, and use this as a multiplier. More accurately again, one may use 2D geometry in each face to estimate the fraction of surface area of E that is both in E and to the desired side of the threshold, and return $h_x h_y h_z$ times this fraction. (This is equivalent to a surface model for each surface area that places a vertex in the middle of E, and creates a surface triangle for each straight edge in a face.) Most accurately, one may construct a triangulated surface independently for each surface area, add vertices and edges where the edges and faces of these surfaces intersect, add triangles to fill in the resulting network of edges, and compute the volume enclosed. This makes the code more complex, but for a small number of doubly-boundary elements it does not greatly increase computation time except in an implementation where all elements treated in parallel in a given step must be completed before the next parallel step begins, where processors which have quickly resolved simple cases would have to wait for the completion of doubly-boundary element computations.

Where the substrate itself is in motion (for example, a heart or lung), the segment S need not be a static region in (x,y,z)-space, but may be a region S (t) that depends on time. The implementation thus requires a representation of moving regions.

Rates of Change

Where the superstrate density is a function c (x,y,z,t) of both position and time, it is often important to report total changes and their rates. In a setting with neither noise nor quantization error, the integral over a region S of the rate of change of density is identical to the rate of change of the integral of density over S. In practice, since rate of change estimation is noise sensitive, this identity depends on the estimation and smoothing methods used. In the present invention, for reasons of numerical efficiency, the preferred implementation is first to compute estimates of "density within range" volume and of superstrate total quantities at the available times t, and then to estimate their rates of change by fitting smooth functions of t to the resulting sequences of scalar values. For numerical integration, these functions are typically evaluated at a mesh of grid points (i,j,k).

Software Structure

In one embodiment, the present invention does not constitute stand-alone software with an end-user interface. It can provide important functionality to a volume-exploration program, which also provides rendering routines for display of surfaces and volumes, and a set of mousepad or reach-in widgets for the user to control what is shown. It provides essential functionality to control software for image-guided delivery of drugs or living cells, as in U.S. Pat. Nos. 6,061,587 and 6,026,316, with needs in its display functions and user interface that overlap with, but are distinct from those of a general volume-exploration program. It could provide essential functionality to (as a hypothetical example) software able to address time-sequenced three-dimensional scans of a hundred rats breathing contrast-labelled tobacco smoke—thousands of volume scans, in all—and return statistics on the depth of penetration at particular smoke particle densities, with no user viewing of individual images.

In another embodiment, the method is implemented as a software library, with an application-programming interface (API) that may be used by any application, such as those just mentioned. The fundamental software object is the "Quantifier" class 600 shown in Drawing 6, which has data members 610 and function members 630. Any valid Quantifier 600 must have specified dimensions 611 I, J, K, for the array which contains the superstrate density values, and know the type 612 of number (integer, floating point, etc.) which is stored there, and the address 613 of the array in which superstrate densities are stored. These members may be defined for it by member-setting functions 640, which may take a variety of arguments, acted on in different ways. (For example, if the function that sets the superstrate array receives a file name or Uniform Resource Name as argument, it will allocate memory and read the data into it. If it receives the address of data already in RAM and accessible for fast computation, it will not make a new copy, but simply store the address. Since no member function in the class modifies the superstrate data, an application using or generating such an array for other purposes may expose it to a Quantifier object 600 without risk.) Where multiple method options exist, as in the choice of how to perform integration or volume estimation, these are specified by flags 614. Member-setting functions 640 may modify either the default or particular values of these flags.

Without valid members of the above types, the Quantifier object 600 is not a valid object. Other data members are needed only for certain functions and may be assigned as necessary. There are optionally assigned arrays 615 for bound density and 616 for free density. The arrays 617 for binding rate and 618 for creation rate are most often used in the context of sequential data, but are available for a single Quantifier object 600. If segmentation software has classified the points in the grid according to enumerated classes $s_1$, $s_2$, . . . , then an application may make an I×J×K array 619 of corresponding classifiers available to the Quantifier object 600, communicating its address with a member-setting function 630. If another function in the application has constructed triangulated surfaces for any of the resulting segments, or other surfaces of interest, the function may provide a list 620 of pointers to such surfaces.

The function of the invention may also provide a pointer 621 to a transport model, such as those discussed in (copending U.S. Ser. No. 09/566,478) which transport model is applied to a function in a standardized format to give the predicted vector of flow at a point (represented by the example of D·∇c in an above equation, so that the Quantifier can compute flow through a surface without itself containing a fixed transport model. Similarly, solving an equation such as (16) for c, given the right hand side, is a service to be provided by the transport model, which is equipped with the appropriate explicit form for the left hand side. The quantifier object does not and need not "know" whether the transport consists of pure diffusion or includes net fluid flow, or the values of such coefficients as D.

The function members 630 of a Quantifier object 600 act on the data it contains. The volume-in-range functions 631 computes the volume of the region in which the superstrate density c lies between limits $C_0$ and $C_1$, within the domain of the data as default, or within a specified segment or surface, from the list 611 or elsewhere. Where the default lower limit 0 or default upper limit ∞ is used, which a density value cannot lie outside, the associated computation may be skipped. Optional arguments, taking default values if unspecified, are shown in square brackets [ ]. The function performs the computation by one of the methods shown in Drawing 8, or by another method added within the architecture of the present invention, according to the method flag 614 currently in place. The integration function 632 returns an estimate of the total quantity of a superstrate with density $c_g$, within the domain of the data or within a specified segment or surface, from the list 620 or elsewhere. The function performs the computation by one of the methods shown in Drawing 9, or by another method added within the architecture of the present invention, according to the method flag 614 currently in place. Given as argument the address of a triangulated surface, either previously declared segment surface or an arbitrary surface in the same format, the surface integration function 633 computes the flux through the surface, as shown in Drawing 10. The difference function 634 computes the point-wise difference between the data array 613 of the Quantifier 600 and the subtrahend 635 to be subtracted from it, with optional arguments that can restrict the computation to a particular segment, specify a divisor (such as the size of a time step) to applied to the difference before storing it, and give a target array (rather than an automatically created new array) or a complete Quantifier object 600 where the results are to be stored. A generalized version 636 allows the application programmer to specify a list of arrays and the code address of an algorithm to be applied to their entries, for such purposes as constructing a Kalman filter to be applied to a sequence of data arrays. An image processing function 637 allows specification of the code address of a local operator such as a discrete Laplacian or an edge detector; a library of commonly-used operators is included, and may be referenced by name. Since an edge detector may return different values of edge strength in different directions, the library and API include a vector-array class to receive such values.

Drawing 7 shows the Temporal Quantifier object 700 that handles a temporal sequence of volume data sets, whether arising by scan or by simulation. To do so, its data members 710 include sequences of members corresponding to single members of a static Quantifier object 600. It also contains corresponding timeless members: array dimensions 711, scalar type 714, method choice flags 716 and transport model 722. Being identical to the corresponding members of a static Quantifier 600, in one embodiment these timeless members are inherited from a common "abstract" C++ class. In a Java implementation of the present invention, however, the Quantifier and Temporal Quantifier objects 600 and 700 would be coded separately. Additional members specific to the temporal case are the number 712 of instants for which datasets (in a common array size and scalar type) are to be analyzed, and the times 713 of those instants. The data arrays 715 are now a list, one for each of the times 713. If segmentation 721 is static, with the substrate segmented in the same way throughout an analysis, it may be represented by a single array: if it is dynamic (as is necessary, for example, in the study of diffusion through a moving lung), it must be represented by arrays for each time.

By default, the volume, integration and efflux functions 731, 732 and 733 respectively produce the sequences of N values that would result from applying those in the static Quantifier 600 to the N arrays in sequence: an optional argument, applicable also to the other function members 730 of a Temporal Quantifier object 700, allows selection of a restricted range or subset of times. These functions yield sequences of numbers: further functions 734, 736 and 737 store results in sequences of target arrays, creating created new array sequences for this purpose if necessary, or in complete Temporal Quantifier objects 700, as specified by the way the function is called. The rate of change function 734 makes use of the subtraction function 634, and its generalization 736 correspondingly exploits the multi-image function 626 in a sequential manner. The operator 738 in the sequential version 737 of the image processing function 637 may refer to data points by spatial offset from a current point within the current data array, by temporal offset in the sequence of arrays, or by a combination of such offsets.

A group 740 of member-setting functions allow fixing or changing of the various data members of the Temporal Quantifier object 700.

Drawing 8 shows the logic which implements formula (10) for the volume contained in a triangulated surface, on the assumption that the surface is topologically closed (each edge is shared by exactly two triangles). The function implementing this logic receives a triangle list as input, and initializes 800 an iteration procedure to the first triangle and a floating point number Volume 6 to 0.0. It reads the (x,y,z) coordinates of the current triangle σ, as in (9), evaluates 810 the expression $$((x_1(\sigma)-x_0(\sigma))(y_2(\sigma)-y_0(\sigma))-(x_2(\sigma)-x_0(\sigma))(y_1(\sigma)-y_0(\sigma)))(z_0(\sigma)+z_1(\sigma)+z_2(\sigma)),$$

adding it to Volume 6, and checks 820 whether this is the last triangle. If No, it goes 821 to the next triangle given by the iterator; and repeats step 810; if Yes, it returns 850 the accumulated Volume6, divided by the common factor 6.0, as the contained volume.

A coarse estimate from the sampling $c_g$ of the volume for which c is between $C_1$ and $C_2$ follows the flow shown in Drawing 9. The function implementing this logic receives array details, the values of $C_1$ and $C_2$, and optionally the details of a segment S. It sets up 900 an iterator over points that may be in S, given the information (bounding box, octree, etc.) in the segmentation data, and initializes an integer counter to 0. It tests 910 the current point for lying between $C_1$ and $C_2$, and optionally 911 for being a point of the segment S. (The order of these steps may be reversed, depending on efficiency considerations depending on the architecture of the central processor and on the fraction of not-in-S points that may be presented by the iterator.) If the point is in range and (optionally) in S, the count is increased 912 by 1. The iterator then tests 920 whether this is the last point: if not, it moves 921 to the next, and repeats the tests 910 and/or 911. If there are no more points, it returns 950 the value of the count, multiplied by the volume $H=h_x h_y h_z$ of the unit volume element. A similar logic flow estimates the quantity of superstrate represented by a density c(x,y,z) over a segment S, replacing the integer count increment 912 by addition of the floating point number c(x,y,z) or a more sophisticated (and numerically costly) estimate of the local contribution to the total. The preferred embodiment of the present invention uses simple addition at this point.

A more accurate volume estimate follows the logic shown in Drawing 10. For simplicity, we show here the version that computes the volume of the region where c(x,y,z) is above (or below, according to a flag set as the function is called) a single threshold C. For the volume between $C_1$ and $C_2$ one may either separately compute the volume below each value and subtract the first from the second, as detailed in Drawing 12, or (where the time of memory access to obtain values of c (x,y,z) is important) duplicate the three steps 1010, 1020 and 1030 below, either adding their difference to the volume accumulator V or maintaining two such accumulators and subtracting one from the other after all volume elements have been processed. The function initializes 1000 an iterator on the first 8-cornered volume element (note that an I×J×K grid has IJK points but only (I−1)(J−1)(K−1) such elements), and sets the floating point number V to 0.0. In step 1010 it determines which case T of the 256 cases shown (up to rotation and—where permitted—reversal) in Drawing 5 matches the combination of in-range and out-of-range corners of the current volume element. Representing the state of each by a 0 or 1, in a determined sequence, this combination corresponds to an 8-bit number, which is used to index a look-up table to select the code used in step 1020 to compute the linear or other interpolation the edge lengths between in-range and out-of-range corners appropriate for this case, and the polynomial from (11) in which step 1030 inserts them to evaluate the contribution that it adds to the volume V. Step 1040 of the iteration determines whether a next element must be found 1041 passed to step 1010; if not, step 1050 multiplies the accumulated V by $H=h_x h_y h_z$ and returns the result.

Where the required quantity is the volume within a segment S for which the value of c (x,y,z) is above C, the logic is slightly more complex. The function computing this quantity receives the details of S and the value of C, and 1100 sets up an iterator over volume elements that may be in S, also initializing a volume estimate to 0.0. It tests 1105 whether all corners of the current volume element are outside S, and if so passing control to the iterator test 1140 of whether any more elements remain. It then tests 1106 whether all corners are inside S; if so, control passes to a sequence 1110, 1120, 1130 of steps identical to 1010, 1020 and 1030 respectively. If not, it computes 1107 a fractional contribution by a method such as one of those described above.

As in the case of the volume computation without reference to a segment S, where the volume of points such that $C_1 < c(x,y,z) \leq C_2$ is required we may use the iterator over volume elements once, computing separately the volumes below $C_1$ and below $C_2$ for each element and adding them to distinct running totals, subtracting one from the other at the end, or adding their difference to a single total. Alternatively, as in Drawing 12, we may 1200 input the data, independently set range conditions "$<C_1$" and "$\leq C_2$" in steps 1210 and 1211 respectively, apply 1220 and 1221 the whole process FV and FV' represented respectively in Drawing 10 or 11 with these inputs, and 1250 report the difference of the two results.

Given grid values of c at two or more successive time points, numerous methods exist for estimating dc/dt, of which the simplest is to subtract the most recent value at each point from the current value there, and divide the result by the time difference. This is equivalent to a straight line fit at each grid point. More complex methods allow fitting of more complex curves to a longer sequence of values, and smoothing across neighboring points. In the present invention we choose one of these available methods and implement it both as a callable function in the API and as step 1310 of the logical flow shown in Drawing 13 of a function which estimates the unbound portion $c^f$ of a measured density $c_g$. The function stores this estimate in an array with address D, then selects 1320 a boundary B within which are above-noise values of c but on which c is negligible or (if no such B exists) throws an exception. It fixes 1330 the address A of an array a (creating the array if necessary, or accepting an address passed to it) in which values of $c^f$ are to be stored. It passes 1340 the data D, A and B to a transport model function which is required to fill a with estimated values of $c^f$ by inverting the transport operator, and upon a successful return from this function returns 1350 the address A.

Another function in the present invention that requires cooperation by the transport model is the computation of flux through a triangulated surface. Its input is a list of N triangles, typically but not necessarily those in a closed surface such as the boundary of a segment, with the vertices of each listed in anticlockwise order as seen from outside. As shown in Drawing 14, it begins 1400 by creating an array e of N+1 scalar values, initialized to 0.0. It initializes (step 1410) to 0 the index I of the current triangle in the input list and the current scalar in the array e. It defines 1420 edge vectors $u_1$ and $u_2$ by subtracting the coordinates of the zeroth vertex of the current triangle from those of the first and second respectively, and computes 1430 the mid-point w of the current triangle. It then 1440 passes w to the transport model, receiving 1441 the flow vector F returned by the transport model for that point. It computes 1450 the estimate w·F of flux through triangle I, adding it to the final number in the array e (which does not correspond to an individual triangle) and storing the resulting per-area flux in e[i] (for uses such as display). It tests 1460 whether there is another triangle in the list, if so advancing 1461 to the next triangle (by incrementing I) and returning to step 1420, otherwise returning the address of e. Alternatively, if the calling function creates the array e and supplies its address as input, the function here described may return only a signal of successful completion.

The invention is particularly useful within medical procedures for determination of a specific administration therapy that should be provided. A volume of the body of the patient is volumetrically evaluated, the available locations or a specific location is assumed, the dynamic response (migration, movement, dispersal, absorption, adsorption, etc.) of administration of a material (e.g., drug, marker, toxin, cell, etc.) at a specific point or at the various points is interpreted or estimated or quantified (hereinafter collectively referred to as "determined") on the basis of the volumetry analysis or evaluation, and a therapy is selected on the basis of results of the interpretation, estimation or quantification. That determined therapy may then be considered for use, and ultimately used upon approval of the determined therapy or procedure.

What is claimed is:

1. A method for supplying a unified suite of quantification functionality for density functions defined in a three-dimensional space including the use of two or more of the services selected from the group consisting of:
   (a) a service computing the volume of a region where a density lies above a specified threshold, below a specified threshold, or between two specified values;
   (b) a service computing an integral of a density;
   (c) a service computationally estimating a rate of change of a density with respect to time;
   (d) a service computationally estimating a local or global failure of conservation of a superstrate within the region represented by changes with time in density;
   (e) a service computationally estimating of a local or global rate at which material with a changing density is passing through a specified surface within the region or at a boundary of the region; and
   (f) separating of density of a material into free and bound densities with a changing density; and
   displaying the results of the selected service.

2. The method of claim 1 wherein the density function in at least one service varies in time.

3. The method of claim 1 wherein the density function in at least one service does not vary in time.

4. The method of claim 1 comprising the use of service (c), wherein service (c) is restricted to a specified region.

5. The method of claim 1 comprising the use of service (d), wherein estimation of local or global failure of conservation is performed with an implemented transport model.

6. The method of claim 1 comprising the use of service (e), wherein estimation of the global rate or local rate at which a superstrate with a changing density is passing through a specific surface is performed with an implemented transport model.

7. The method of claim 1 wherein at least two services used in the method each yields an answer for restriction of a density to a specified region.

8. The method of claim 1 where a density is obtained by a three-dimensional scanning process.

9. The method of claim 1 wherein a density is obtained by a numerical simulation process.

10. The method of claim 1 wherein a density is obtained by an algorithm specification.

11. The method of claim 1 comprising the use of service (a), wherein the volume in (a) is computationally estimated by counting grid points.

12. The method of claim 1 comprising the use of service (a), wherein the volume in (a) is estimated by approximation within eight-cornered volume elements.

13. The method in claim 12 wherein the approximation within said eight-cornered volume elements is performed by fitting a boundary surface to interpolated edge points of said volume elements.

14. The method of claim 1 comprising the use of service (a), wherein the volume in (a) is computationally estimated by finding the volume contained in a triangulated surface approximating the boundary of said region.

15. The method in claim 14 where the volume contained in said surface is computed by summing signed volumes of prismatic domains obtained by projecting triangles parallel to a coordinate axis.

16. The method of claim 1 comprising the use of service (b), wherein the integral in (b) is computationally estimated by summing density values at grid points.

17. The method of claim 16 wherein a grid point near an edge of a region of restriction contributes a value weighted by a fraction of an immediate neighborhood of a grid point that is in the said region.

18. The method of claim 16 wherein the integral in (b) is computationally estimated by fitting local approximations to the density and summing integrals of these approximations.

19. The method of claim 18 wherein a local approximation near the edge of a region of restriction contributes its integral over part of its domain that is in said region.

20. The method of claim 1 wherein said density comprises a concentration of a drug or other molecular substance in an organism.

21. The method of claim 1 wherein said density refers to the concentration of a class of cell in an organism.

22. The method of claim 1 wherein said density refers to the concentration of microscopic devices inserted into an organism.

23. The method of claim 20 wherein said organism is a human body.

24. The method of claim 21 wherein said organism is a human body.

25. The method of claim 22 wherein said organism is a human body.

26. The method of claim 20 wherein said region is within a human brain.

27. The method of claim 21 wherein said region is within a human brain.

28. The method of claim 22 wherein said region is within a human brain.

29. The method of claim 1 wherein the density represents molecules, cells or devices inserted into an organism, body or brain for therapeutic purposes.

30. The method of claim 29 wherein said density is obtained by simulation of the transport and action of said molecules, cells or devices.

31. The method of claim 20 wherein said density within the body, and said molecules or cells are part of a normal process or disease process.

32. The method of claim 1 wherein said density refers to a material being transported by a geological process.

33. The method of claim 1 wherein said density refers to a material moving through a structure created by human agency.

34. The method of claim 1 wherein said density is a mathematical construct convenient in defining three-dimensional shapes for the purposes of computer-aided design.

35. A method for effecting a therapy upon a patient using the method of claim 1 to volumetrically evaluate a volume of a body of the patient by assuming available locations or a specific location for introduction of a therapy, evaluating the dynamic response over time on the basis of the volumetric evaluation, and selecting a therapy on the basis of results of the estimating.

36. The method of claim 35 wherein the selected therapy is then approved for use on a patient.

37. The method of claim 36 wherein the selected therapy is performed on the patient.

38. A method for supplying a unified suite of quantification functionality for density functions defined in a three dimensional space and dynamically in time for that three-dimensional space including the use of two or more of the services selected from the group consisting of:
   (a) a service computing the volume of a region where a density lies above a specified threshold, below a specified threshold, or between two specified values;
   (b) a service computing an integral of a density;
   (c) a service computationally estimating a rate of change of a density with respect to time;
   (d) a service computationally estimating a local or global failure of conservation of a superstrate within the region represented by changes with time in density;
   (e) a service computationally estimating a local or global rate at which material with a changing density is passing through a specified surface within the region or at a boundary of the region; and
   (f) a service separating of density a material into free and bound densities with a changing density; and
displaying the results of the selected service.

* * * * *